(12) United States Patent
Kim

(10) Patent No.: US 8,211,470 B2
(45) Date of Patent: Jul. 3, 2012

(54) METHOD FOR PREPARING NANO-SCALE OR AMORPHOUS PARTICLE USING SOLID FAT AS A SOLVENT

(75) Inventor: Kab-Sig Kim, Seoul (KR)

(73) Assignee: Bio-Synectics Inc. (KR)

( * ) Notice: Subject to any disclaimer, the term of this patent is extended or adjusted under 35 U.S.C. 154(b) by 1720 days.

(21) Appl. No.: 10/596,178

(22) PCT Filed: Nov. 11, 2004

(86) PCT No.: PCT/KR2004/002914
§ 371 (c)(1),
(2), (4) Date: Jun. 2, 2006

(87) PCT Pub. No.: WO2005/054122
PCT Pub. Date: Jun. 16, 2005

(65) Prior Publication Data
US 2007/0071826 A1    Mar. 29, 2007

(30) Foreign Application Priority Data

Dec. 5, 2003    (KR) ........................ 10-2003-0088303
Nov. 9, 2004    (KR) ........................ 10-2004-0090832

(51) Int. Cl.
*A61K 9/14*    (2006.01)
(52) U.S. Cl. ..................................................... 424/489
(58) Field of Classification Search .................... None
See application file for complete search history.

(56) References Cited

U.S. PATENT DOCUMENTS

| 6,264,933 B1 | 7/2001 | Bodelin et al. | |
| 6,471,993 B1* | 10/2002 | Shastri et al. | 424/486 |
| 2004/0043076 A1* | 3/2004 | Dulieu et al. | 424/490 |
| 2006/0035350 A1* | 2/2006 | Catchpole et al. | 435/134 |

FOREIGN PATENT DOCUMENTS

| JP | 3-30603 | 2/1991 |
| JP | 7-184556 | 7/1995 |
| JP | 11-255602 | 9/1999 |

OTHER PUBLICATIONS

International Search Report for PCT Application No. PCT/KR2004/002914.

* cited by examiner

*Primary Examiner* — Paul Dickinson
(74) *Attorney, Agent, or Firm* — Sheridan Ross P.C.

(57) ABSTRACT

The present invention relates to a method for preparing nanoscale or amorphous particles using solid fat as a solvent. According to the present invention, nanoscale or amorphous particles of active ingredients are prepared by using fat as a solvent, wherein the fat is in solid phase at room temperature. The nanoscale or amorphous particles of active ingredients can be advantageously used in medicine, cosmetics, functional foods or the like.

17 Claims, No Drawings

METHOD FOR PREPARING NANO-SCALE OR AMORPHOUS PARTICLE USING SOLID FAT AS A SOLVENT

TECHNICAL FIELD

The present invention relates to a method for preparing nanoscale or amorphous particles using solid fat as a solvent. Specifically, the present invention relates to a method for preparing nanoscale or amorphous particles of active ingredients which are advantageously used in medicine, cosmetics, functional foods or the like, by using fat in solid phase at room temperature as a solvent.

BACKGROUND ART

A demand for a technique of an effective and rapid preparation of very fine particles in regular size has been constantly required in various industrial fields. Such fine particles in regular size have many advantages, particularly among which good flowability and little deviation in particle interaction are very advantageous in industrial application. In medical field, the particle size of a therapeutic agent greatly affects to the dissolution rate, bioavailability, formulation and the like, and for example, the smaller the deviation in the interaction between the particles of a therapeutic agent is, the better the whole stability of the therapeutic agent becomes.

When the particle of a therapeutic agent is made into nanoscale size in medicinal products, following advantages may be obtained. First of all, in a drug having a small enteral absorption rate in oral administration, one having a smaller size can be absorbed more than one having a bigger size, thereby increasing the bioavailability of the therapeutic agent. Further, the dosage form of drugs can be varied, for instance a drug being possibly administered only via oral route can be administered by inhalation. In a controlled-release drug formulation, the release rate of a therapeutic agent is a very important factor. When the particle size of the therapeutic agent is formed to be in nanoscale, the particle size becomes relatively more uniform, thus the release rate can become more expectable, thereby being possible to provide more effective therapeutic agent.

In order to take various advantages of regular nanoparticles as described above, many attempts have been made to prepare an active ingredient as a nanoparticle. For this object, mechanical techniques such as crushing, grinding, milling and the like have been conventionally employed to make relatively large particles smaller. In the pharmaceutical industry, a method of milling a mass amount of drugs to the size range being suitable for the medicinal or pharmaceutical use with an air-jet mill has been commonly used. However, such mechanical process involves the risk of contamination and had a limitation on decreasing the particle size to about tens of micrometers.

U.S. Pat. No. 5,145,684 discloses a method for preparing particles of poorly water-soluble drugs in the size of hundreds of nanometers by wet milling the poorly water-soluble drugs in the presence of a surface modifier. This technique should be applied after a preparation of the drugs in the particle size of not more than 100 micrometer by using a conventional milling process. Generally in this method, the time taken for the preparation of particles having a targeted size range depends on the particular mechanical device used thereto. For example, when using a ball mill, processing times of up to 5 days or longer may be required, however, when using a high shear media mill, 1 day would be enough to provide particles of a desired size. However, in connection with the use of a high shear media mill, contamination associated with the high corrosion of grinding media and grinding vessel should be concerned. Further, a drying process such as spray or freeze drying should be conducted for getting powder form, because the resulted nanoparticles from the wet milling method are in liquid phase. During the drying process, coagulation of the particles is occurred due to interparticle attraction forces, hence it is substantially difficult to obtain a dispersion of particles in a nanometer scale by redispersing the resulted powder into a liquid. In order to solve such problem, U.S. Pat. No. 5,302,401 describes an anti-coagulating agent employed during lyophilization. Additionally, U.S. Pat. No. 6,592,903 B2 describes an invention comprising a stabilizer, a surfactant and an anti-coagulating agent used during a spray dry process. Further, US Patent No. 2003/0185869 A1 describes an application of a wet milling technique for some poorly soluble drugs, with using lysozyme as a surface stabilizer. However, such protein surface stabilizer used therein has many restrictions in a drying process, accordingly it only describes the preparation in liquid phase.

Other conventionally available methods include a recrystallization technique which provides fine particles of an active ingredient by changing the environment of a solution containing dissolved active ingredient to cause the precipitation or crystallization of solutes. The recrystallization technique can be practiced in two different ways: the one being comprised of dissolving a therapeutic agent in a suitable solvent and lowering the temperature, thereby changing the solubility of the therapeutic agent to precipitate particles; and the other being comprised of adding antisolvent to a solution containing dissolved therapeutic agent, thereby decreasing the solubility of the solute to precipitate particles. However, the recrystallization technique usually requires the use of toxic organic solvent and often causes flocculation or coagulation of the particles during a drying process in wet condition, following after the filtration of the precipitated particles. As a result, the final particles may be irregular in their size.

US Patent No. 2003/0104068 A 1 discloses a method for preparing fine particles comprising: dissolving polymers into an organic solvent; dissolving or dispersing a proteineous drug thereto; then rapidly cooling the solution to ultra-low temperature for solidification; and lyophilizing the resulted product to provide a fine powder. In this case, however, there are concerns for the denaturation of a proteineous drug by the contact with an organic solvent and the process economy owing to the rapid cooling and lyophilizing process.

Other techniques for reducing particle size include emulsification. The emulsifying method is commonly used in cosmetic field, which comprises melting poorly water soluble substances with heat or dissolving them in an organic solvent, and then adding the melted or dissolved substances to an aqueous solution containing a surfactant dissolved therein, with stirring at high speed or with sonication to disperse the added substances and provide fine particles. However, in this emulsification method, a step for removing water is required for providing the fine particles in a powdered form, and the step gives variously restrictions to the process. Further, when using an organic solvent to dissolve the poorly water-soluble substance, there always has been a concern for residual toxic organic solvent.

US Patent No. 2004/0067251 A1 discloses a method for preparing fine particles by dissolving active ingredients into an organic solvent and spraying the resulted solution to an aqueous solution containing a surfactant dissolved therein. The invention involves the use of an organic solvent, and requires a drying process for removing the water used, to provide the particles as a powdered form, since the resulted particles are present in aqueous phase. During the drying process, the coagulation of the particles is likely to be occurred, hence the coagulated particles are hardly redispersed with maintaining the particle size to a nanoscale.

Recently, many attempts have been made to use a supercritical fluid in the amorphous or nanoscale particle preparation. Supercritical fluid is a fluid existing in liquid form at a temperature higher than its critical temperature and under pressure higher than its critical pressure. Commonly used supercritical fluid is carbon dioxide. As one of techniques involving the use of supercritical fluids in a nanoparticle preparation, the rapid expansion of a supercritical solution (hereinafter, RESS) is known from the following literatures: Tom et al. *Biotechnol. Prog.* 7(5):403-411. (1991); U.S. Pat. No. 6,316,030 B1; U.S. Pat. No. 6,352,737 B1; and U.S. Pat. No. 6,368,620 B2. According to RESS, an object solute is firstly dissolved in a supercritical fluid, and then the supercritical solution is rapidly sprayed into a relatively low-pressure condition via nozzle. Then, the density of the supercritical fluid rapidly falls down. As a result, the ability of the supercritical fluid to solubilize the solute is also rapidly reduced, and the solutes are formed into very minute particles or crystallines.

Other techniques using a supercritical fluid include a gas-antisolvent recrystallization (hereinafter, GAS) (Debenedetti et al. *J. Control. Release* 24:27-44. (1993); WO 00/37169). The method comprises dissolving a therapeutic agent in a conventional organic solvent to prepare a solution and spraying the resulted solution into a supercritical fluid served as an antisolvent, through a nozzle. Then, the volume becomes rapidly expanded upon the contact between the solution and the supercritical fluid. As a result, the density and capacity of the solvent become so much lower to cause excessive supersaturation, hence the solutes form seeds or particles.

U.S. Pat. No. 6,630,121 describes a method for preparing fine particles by nebulizing a solution containing active ingredients to provide fine particles with the use of a supercritical fluid, and drying the resulted particles with a dry gas. The method can be used regardless of the solubility of the active ingredients to the supercritical fluid. WO 02/38127 A2 describes a method using SEDS (Solution Enhanced Dispersion by Supercritical fluids) technique for preparing fine particles of active ingredients and coating the resulted fine particles with an additive such as a polymer. Further, U.S. Pat. No. 6,596,206 B2 describes a technique of preparing fine particles of active ingredients by dissolving the active ingredients in an organic solvent and focusing acoustic energy to the resulted solution so that the solution can be ejected into a supercritical fluid as a form of fine particles.

DISCLOSURE

Technical Problem

Those above-mentioned prior arts propose a method for producing very fine particles with relatively uniform size, but have several disadvantages.

The first disadvantage is likely to occur in a tube for transferring a solution and a nozzle. In a preparation method of fine particles using a supercritical fluid, the particle size generally determined by the diameter of a nozzle used in the method, accordingly the diameter of a nozzle ought to be very fine and precise. However, upon the repeated use of a nozzle, the diameter of the nozzle becomes changed, hence the particle size becomes irregular as time elapses. Moreover, due to the use of a nozzle having an ultra-fine diameter for the preparation of ultra-fine particles, the clogging of the nozzle is likely to occur very often. Further, during unclogging of the nozzle, caking of the particles remained in the tube is frequently occurred.

The second disadvantage of the prior arts is that the species of solutes applicable and solvents available are very limited. The RESS technique can be suitably applied only provided that the solutes are well dissolved in a supercritical fluid. Depending on the solutes, the solubility thereof is possibly increased with the use of a co-solvent, however, if the amount of co-solvent increases, the existence of the residual solvent after the particle generation would cause the growth of crystals, which obstructs the preparation of the particles in regular size. In the GAS technique, a solvent should be selected with great concern. Only provided that the solvent containing the solutes dissolved therein is rapidly diffused into the supercritical fluid as being contacted together, fine particles can be generated. Further, the growth of particles can be prevented, provided that the amount of solvent remained between the particles during filtration is minimized. In addition, the GAS technique requires a special filtration device for filtering the resulted fine particles from the solvent.

The third disadvantage of the prior arts is that there are many restrictions in commercial scale production of nanoparticles by those conventional methods using a supercritical fluid. For the commercial scale use of RESS, solutes used should be very soluble in a supercritical fluid, which are very rare. Further, the preparation of nanoscale fine particles of a single species of material involves the coagulation of the particles, hence an anti-coagulating material such as an emulsifier, cellulose or lipids should be dissolved together, and the mixture thereof should be made into fine particles in nanoscale. However, most of the anti-coagulating materials would not be soluble in carbon dioxide which is mainly used as a supercritical fluid. In preparing nanoparticles using GAS, the solution containing solutes dissolved therein is injected into a reactor containing a supercritical fluid, but the injection rate is so slow that the preparation of uniform-sized particles is difficult. However, when increasing the injection rate, the particle sizes become irregular and further problems would be occurred in a filtration process. Moreover, the resulted particles with the composition ratio, which was not originally intended, would be obtained instead of particles with desired composition ratio, due to the differences between the solubility of the solutes to the solvent and the solubility of the anti-coagulating material added thereto, for preventing the coagulation of particles.

Technical Solution

The present invention is designed to solve those problems of the prior arts as described above. The object of the present invention is to provide a method for preparing nanoscale or amorphous fine particles of active ingredients which uses a supercritical fluid for preparation nanoparticles, wherein the method comprises preparing a mixture including active ingredients and solid fat and then removing solid fats therefrom with a supercritical fluid.

Mode of Invention

According to the present invention, provided is a method for preparing nanoscale or amorphous particles, comprising the steps of: (1) preparing a mixture comprising one or more active ingredients and solid fat and (2) pressurizing the mixture comprising one or more active ingredients and solid fat to the critical pressure or more by adding the gas of a supercritical fluid into the mixture, and then removing the solid fat from the mixture by releasing out the solid fat together with the gas of the supercritical fluid.

According to one preferred embodiment of the present invention, the step (1) comprises: adding one or more active ingredients, solid fat and optionally one or more surfactants into a reactor and melt-mixing them homogeneously.

According to other preferred embodiment of the present invention, the step (1) comprises: adding one or more active ingredients, solid fat and optionally one or more surfactants into a reactor and melt-mixing them homogeneously; rapidly cooling the mixture for solidification; pulverizing the solidified mixture; adding one or more surfactants and/or one or more non-surfactant type anti-coagulating agents or aqueous solution thereof to the pulverized powder and mixing them homogeneously; and drying the mixed product at room temperature.

According to another preferred embodiment of the present invention, the step (1) comprises: adding one or more surfactants and solid fat into a reactor, and melt-mixing them homogeneously; rapidly cooling the mixture for solidification; pulverizing the solidified mixture; adding one or more surfactants and/or one or more non-surfactant type anti-coagulating agents together with one or more active ingredients or aqueous solution thereof, to the pulverized powder and mixing them homogeneously; and drying the mixed product at room temperature.

According to another preferred embodiment of the present invention, the step (1) comprises: adding one or more active ingredients, solid fat and optionally one or more surfactants into a reactor, further adding the gas of a supercritical fluid so as to provide a subcritical or supercritical condition, and then melt-mixing the mixture by heating.

According to another preferred embodiment of the present invention, the step (1) comprises: adding one or more active ingredients, solid fat and optionally one or more surfactants into a reactor, pressurizing the mixture to the critical pressure or more by adding the gas of a supercritical fluid into the mixture and then melt-mixing the mixture by heating, and spraying the melted mixture to the atmospheric pressure.

According to another preferred embodiment of the present invention, the step (1) comprises: adding one or more active ingredients, solid fat and optionally one or more surfactants into a reactor, pressurizing the mixture to the critical pressure or more by adding the gas of a supercritical fluid and then melt-mixing the mixture by heating, and pulverizing the melted mixture by spraying it to the atmospheric pressure; adding one or more surfactants and/or one or more non-surfactant type anti-coagulating agents or aqueous solution thereof to the pulverized mixture and mixing them homogeneously; and drying the mixture at room temperature.

The term "gas of a supercritical fluid" used herein, refers to an inert gas, which has no reactivity such as a carbon dioxide gas or a nitrogen gas, but can be a supercritical fluid under specific temperature and pressure conditions, i.e. beyond their critical point.

"Critical pressure" used herein, refers to a specific pressure at least under which the gas of a supercritical fluid can be liquefied as a supercritical fluid.

The active ingredients useful in the method for preparing nanoscale or amorphous particles (hereinafter, referred as "nanoparticles") according to the present invention include, for example, organic compounds, organometallic compounds, natural extracts, peptides, proteins, polysaccharides and the like, which exhibit specific physiological activities in medicinal products, functional foods, cosmetics and the like, and there is no specific restriction on their phase at room temperature such as solid or liquid phase and electrical properties such as being neutral or ionic.

"Nanoparticles" used herein, refers to particles wherein 90% or more of the particles have a size of 5 $\mu$m or less, preferably 2 $\mu$m or less, more preferably 1 $\mu$m or less, still more preferably 0.5 $\mu$m or less.

The solid fat useful in the method for preparing nanoparticles according to the present invention, is a fat or a mixture of fats maintaining solid phase at room temperature, i.e. at 30° C. or less, having a relatively low melting point as being 40-150° C. Thereby, the solid fat is easily melted with heat and is served as a solvent for the active ingredients. Also, the solid fat is highly soluble in the supercritical fluid. The solid fat includes, for instance, saturated fatty acids, esters and alcohols with C10-C22; mono- or di-glycerides having saturated fatty acid group with C10-C22; hydrocarbons with C16 or more; or a mixture thereof. Further, tri-glycerides with C10-C22 may be used after solidifying them by reducing the fatty acid.

According to the method for preparing nanoparticles of the present invention, the nanoparticles may be prepared by using the active ingredients as a single component. Optionally, an anti-coagulating agent may be further used for preventing the coagulation of the resulted nanoparticles. Such anti-coagulating agents useful in the present invention may be classified into a surfactant type and a non-surfactant type. As the surfactant type anti-coagulating agent, various synthetic and natural surfactants, lipids, polymers and the like may be used. As the non-surfactant type anti-coagulating agent, monosaccharides, polysaccharides, dietary fibers, gums, proteins and the like may be used. Phospholipids such as lecithin, lysolecithin, phosphatidyl choline, phosphatidyl ethylamine and the like are referred herein as a surfactant, though it may be classified as lipids in general. Surfactants may be generally divided, upon their affinity to water, into a hydrophilic and a lipophilic type, which are determined by the HLB (hydrophilic-lipophilic balance) value. Upon the functional groups, there are four types of surfactants such as cationic, anionic, neutral and zwitterionic. A surfactant useful in the present invention is not specifically restricted to a certain type or species, as long as it prevents the coagulation of the active ingredients, and it is well dissolved in the solid fats and is not readily removed by a supercritical fluid.

Further, when sufficient dissolution of the active ingredients and surfactants is not achieved by using only solid fats, one or more alcohols may be further used as a co-solvent in the method of the present invention, wherein the co-solvent is preferably one or more lower alcohols with C2-C6, and ethanol is the most preferred.

Hereinafter, the method for preparing nanoparticles of the present invention is now illustrated step by step with more details.

In the step (1) of the method for preparing nanoparticles according to the present invention, a mixture comprising one or more active ingredients and solid fat is prepared. The details thereof are now described as follows.

According to one preferred embodiment of the present invention, one or more active ingredients and solid fat are added into a reactor wherein the amount of the solid fat is 0.1-1000 parts by weight per 1 part by weight of the active ingredients. At this stage, when necessary, 0.001-10 parts by weight of surfactant or 0.001-10 parts by weight of lower alcohol, or a mixture of 0.001-10 parts by weight of surfactant and 0.001-10 parts by weight of lower alcohol, based on 1 part by weight of the active ingredients may be optionally added to the reactor.

The optionally added surfactant should have relatively large solubility to the solid fats so as to form a homogeneous solution when being dissolved together with the active ingredients in solid fat, or in solid fat containing a lower alcohol described above. Further, different surfactants may be selected, depending on the properties of the active ingredients and the use or the purpose of use of the resulted nanoparticles. When the resulted nanoparticles are used finally in the form of a water dispersion, a surfactant with a high HLB value is preferably selected, and when the purpose is to increase the internal absorption rate, a surfactant with a relatively low HLB value is preferably selected.

As mentioned above, the active ingredients and solid fat are added to a reactor and when being necessary, surfactant or lower alcohol or a mixture thereof is further added to the reactor, and then the mixture in the reactor is gradually melted as being heated.

As the temperature inside the reactor rises, the solid fat becomes melt, and the active ingredients and surfactant are dissolved or dispersed therein. The temperature is raised until a homogeneous solution or dispersion is formed. It is preferred to start stirring from the point when it becomes possible, since it will make the solution or dispersion of the mixture more homogeneously and reduce the working time. The point when stirring becomes possible, depends on the specific species of the active ingredients, surfactant and solid fat used in the method, however the determination of the starting point of stirring will be easily made at the working site by the skilled person in this field.

According to other preferred embodiment of the present invention, as it has been mentioned above, a mixture comprising one or more active ingredients and solid fat is prepared by: adding the one or more active ingredients, solid fat and optionally one or more surfactants to a reactor; melt-mixing them together homogeneously; rapidly cooling the resulted mixture for solidification; pulverizing the solidified mixture; adding one or more surfactants and/or one or more non-surfactant type anti-coagulating agents or aqueous solution thereof to the resulted powder, and mixing them homogeneously; and drying the resulted mixture at room temperature. In the above processes, the drying process is not particularly restricted to a certain method, but it should be conducted below the melting point of the solid fat used.

According to another preferred embodiment of the present invention, when the active ingredients are those sensitive to the temperature or soluble in water such as peptides, proteins or polysaccharides, the mixture comprising the active agents and solid fats is prepared by: firstly, adding one or more surfactants and solid fat into a reactor and melt-mixing them homogeneously; rapidly cooling the melted mixture for solidification; pulverizing the solidified mixture; then adding the active ingredients together with one or more surfactants and/or one or more non-surfactant type anti-coagulating agents or aqueous solution thereof, to the resulted powder, and mixing them homogeneously; and drying the resulted mixture at room temperature. In the above processes, the drying process is not particularly restricted to a certain method, but it should be conducted below the melting point of the solid fat used.

In the solidification of the mixture by rapid cooling, it is preferred to rapidly decrease the temperature of the solution of the melted mixture to the temperature of 10° C. or less. When cooling is conducted slowly, crystal growth of the active ingredients may occur, and under such circumstances, the nanoparticles of the active ingredients are hardly achieved and the obtained particles are likely to have a broad particle distribution.

The solid product obtained from the rapid cooling, is conventionally milled by, for example, dry milling and the like. The smaller the size of the milled particles is, i.e. the larger the surface area of the particles is, the more it is advantageous in later processes such as a fat removal process. The particle size after the milling process is preferably 100 micrometer or less, but not limited thereto.

According to another preferred embodiment of the present invention, the mixture comprising one or more active ingredients and solid fat is prepared by: adding the one or more active ingredients, solid fat and optionally one or more surfactants to a reactor; further adding the gas of a supercritical fluid (for instance, $CO_2$ gas) to the mixture so as to form subcritical or supercritical conditions; and then melting the resulted mixture by heating.

According to another preferred embodiment of the present invention, the mixture comprising one or more active ingredients and solid fat is prepared by: adding the one or more active ingredients, solid fat and optionally one or more surfactants to a reactor; adding thereto the gas of a supercritical fluid up to the pressure over the critical pressure and melting the mixture; and then spraying the melted mixture to the atmospheric pressure.

According to another preferred embodiment of the present invention, a mixture comprising one or more active ingredients and solid fat is prepared by: adding the one or more active ingredients, solid fat and optionally one or more surfactants to a reactor; adding thereto the gas of a supercritical fluid up to the pressure over the critical pressure and melting the mixture; then spraying the melted mixture to the atmospheric pressure for pulverization; adding one or more surfactants and/or one or more non-surfactant type anti-coagulating agents or aqueous solution thereof to the resulted mixture and mixing homogeneously; and drying the mixture at room temperature. In the above processes, the drying process is not particularly restricted to a certain method, but it should be conducted below the melting point of the solid fat used.

In the case of using a supercritical fluid in the step (1) of the present invention, after the components of the mixture are completely melted and homogeneously mixed, a supercritical fluid such as $CO_2$ is slowly added into a reactor to pressurize the mixture up to the pressure under which the gas of a supercritical fluid is liquefied as a supercritical fluid, i.e. the critical pressure (for $CO_2$, 70 atm) or more. The pressure inside the reactor at this stage depends on the reactor size and the amount of the mixture, but generally preferred is 50-200 atm. The temperature at this stage is a temperature that can provide the sufficient fluidity to the solution of the mixture for stirring.

Once the critical pressure or more is achieved by rising the pressure inside the reactor with the gas of a supercritical fluid, it is preferred to carry out stirring for additional 10 minutes or more at that condition, so that the supercritical fluid may be sufficiently permeated into the solution of the mixture.

In completing the additional stirring, while slowly adding thereto the gas of the supercritical fluid further, the exhaust port connected to another reactor under atmospheric pressure, is opened to the full for spraying the resulted solution of the mixture into the reactor under atmospheric pressure. At this moment, the supercritical fluid is instantly vaporized, thereby rapidly cooling down the surroundings and causing the solidification of the resulted solution of the mixture in an instant. The solidification of the solution of the mixture is so instantaneous that it becomes short of energy and time demanded for crystal growth, therefore it is possible to obtain solid products in which the solutes including the active ingredients, surfactant and the like and the solid fat are homogeneously mixed in the form of very fine particles. In the solid products obtained therefrom, the very fine nanoscale particles of the active ingredients are dispersed uniformly. Further, since the surfactant is also uniformly mixed with the active ingredients, the dispersability and stability of the finally produced fine particles become significantly improved.

The purpose of this step is to make the particles of active ingredients be finer and more uniform in the solid product. Therefore, as long as the particle size of the solid product containing the active ingredients is in the range that does not cause any problem to the workability in later processes, it is not necessary to specifically adjust the particle size of the solid product itself. Accordingly, it is not necessary to adjust the spray nozzle diameter or the spraying rate, in order to adjust the particle size of the solid product itself produced by spraying into the atmospheric pressure condition. Therefore, the risk of deformation or clogging of the spray nozzle does not need to be concerned any more.

In spraying the solution of the mixture into another reactor under the atmospheric pressure condition, a conical supporting plate is preferably placed inside the reactor under the atmospheric pressure condition, at a distance from the spray outlet such as nozzle, in order to solidify the sprayed solution into the form of finer powders. By doing so, the solids can be formed into finer particles, and in the next step, the solid fat can be more easily removed with the supercritical fluid.

According to the preferred embodiment of the present invention, to the powdered mixture obtained by using a supercritical fluid or milling, when being necessary, one or more surfactants and/or one or more non-surfactant type anti-coagulating agents or aqueous solution thereof can be added, or alternatively when the active ingredients are those temperature sensitive or water soluble such as peptides, proteins or polysaccharides, the surfactant and/or the non-surfactant type anti-coagulating agent together with the active ingredients or aqueous solution thereof can be added. The resulted mixture may be homogeneously mixed by using a general mixer. In the above, when necessary, the non-surfactant type anti-coagulating agent is added in the amount of 0.001-10 parts by weight per 1 part by weight of the active ingredients. When the aqueous solution of surfactant or the non-surfactant type anti-coagulating agent is added, the physical state of the resulted mixture may be varied upon the amount of water used and the species of the surfactant and anti-coagulating agent, but if the amount of water added is generally 30% (w/w) or less of the amount of fats used, the mixture will be readily formed into a powder. The amount of water added is not specifically limited, as long as it can sufficiently disperse the water-soluble components into the mixture prepared. When 40% (w/w) or more of water is used, the mixture becomes the form of dough or paste, which can be dried easily at room temperature by various conventional methods. The drying process is not particularly restricted to a certain method, but it should be conducted below the melting point of the solid fat used. Further, it would be readily understood by the skilled person in this field that, the smaller the particle size used is, the more water can be easily removed by a conventional drying process under reduced pressure. After completing the drying process, the residual water content relative to the solid fat content is preferably not more than 30%.

In the step (2) according to the method for preparing nanoparticles of the present invention, the solid fat is removed from the mixture comprising one or more active ingredients and the solid fat, by using a supercritical fluid. The details thereof are described as follows.

While maintaining the temperature of the reactor containing the mixture obtained from the preceding steps including the step (1), in maintaining the temperature below the melting point of the solid fat present in the mixture, preferably maintaining the temperature in the range of 20-40° C., the gas of a supercritical fluid is added to the reactor to pressurize it to 70-400 atm. Then, under said pressure, the gas of a supercritical fluid is gradually released out, wherein the reactor pressure is constantly maintained by controlling an input valve and an output valve for the gas of a supercritical fluid such as carbon dioxide. Along with the release of the gas of the supercritical fluid, the solid fat is also released out, i.e. removed from the reactor. At this stage, if the temperature inside the reactor is too high, the solid fat becomes melt, hence causing the growth of crystal of the active ingredient, surfactant, anti-coagulating agent and the like which were uniformly dispersed in the mixture. As a result, regular nanoparticles are not possibly obtained. For above reason, the reactor temperature is preferably maintained below the melting point of the solid fat present in the mixture, and in terms of workability, more preferred is in the range of 20-40° C.

The time taken for removing the solid fats with a supercritical fluid is quite dependant on the species and amount of the solid fat used. In order to obtain the particles of active ingredients with higher purity, it is preferred to take time in removing the solid fats as long as possible, thereby minimizing the residual amount of the solid fats. The solid fats preferably used in the present invention are non-toxic to a human body, therefore the residual amount is not particularly limited to a specific range. However, considering the purity of the resulted active ingredients, the residual amount is preferably not more than 10 wt % of the total weight. As for exception, when the solid fat such as mono-, di- or tri-glyceride type compounds, which is also generally used as a surfactant, is used, it would be no problem even if the residual amount of the solid fat is more than 10% of the total weight.

The solid fat removed from the mixture by the method described above, can be collected in a separate reactor and then used again in future.

Hereinafter, the present invention is illustrated in detail with a reference to the examples as follows, however the present invention is by no means limited to those examples.

Example 1

A 80 ml pressure-resistant reactor was charged with 2 g of ketoconazole as an active ingredient and 18 g of cetyl alcohol as a solid fat and slowly heated, and stirring was started when the temperature inside the reactor reached to 70° C. When the temperature inside the reactor reached to 80° C. by further heating, the mixture became a homogeneous solution in transparent liquid phase.

Next, the pressure inside the reactor was elevated by adding a carbon dioxide gas as a gas of a supercritical fluid, by opening an input valve for feeding a supercritical fluid. The carbon dioxide gas was continuously added into the reactor until the pressure inside the reactor reached to 120 atm which is over the critical pressure of the carbon dioxide gas. Then, the input valve for feeding a supercritical fluid was closed, and additional stirring was carried out for 20 minutes. Completing the additional stirring, while the carbon dioxide gas was slowly added again by opening the input valve for feeding a supercritical fluid, a spray valve that is connected to a collecting reactor under atmospheric pressure was widely opened all at once so as to spray the solution of the mixture completely. At this stage, a vent valve equipped to a collecting reactor was remained wide open, in order to maintain the atmospheric pressure condition of the collecting reactor. Further, the inside of the collecting reactor was equipped with a conical plate placed in front of the spray nozzle, for providing finer powders from the solution sprayed out from the nozzle. After completing the spraying of the solution, carbon dioxide gas was still fed for additional 10 minutes and then the input and spray valve of the supercritical fluid were closed.

Next, the pressure inside the collecting reactor containing the sprayed solid powders was elevated to about 150 atm by adding carbon dioxide gas into the collecting reactor. The pressure inside the collecting reactor was constantly maintained to the pressure of 100 atm or more by controlling a vent valve of the collecting reactor, while continuously adding the carbon dioxide gas. Under the constantly maintained pressure, the cetyl alcohol used as a solid fat was extracted for 8 hours with the gas of the supercritical fluid to obtain 1.8 g of fat-removed fine solid particles. The particle size of the obtained powdered mixture was determined by a particle size analyzer (Mastersizer Microplus) by dispersing the obtained powdered mixture into distilled water, and the result was shown in Table 1.

Example 2

30 g of cetyl alcohol and 2 g of ketoconazole were placed into a 250 ml volume beaker and heated to 80° C. with stirring until the mixture became completely melt to form a transparent liquid. After completely melting the mixture, additional stirring for about 10 minutes was further carried out for homogeneous mixing. Then, the melted mixture was poured into a stainless steel plate which was precooled to 10° C. or less for rapid cooling and solidifying, thereby obtaining the solid product in which the active ingredient was dispersed uniformly into the fat in the form of fine particles. The resulted solid product was milled into fine particles, together with 2 g of D-(+)-sucrose as an anti-coagulating agent by a domestic milling device, to provide fat powder. 5.5 g of the fat powder was placed into a pressure resistant reactor, and cetyl alcohol used as a solid fat was removed therefrom by the same method as in Example 1 to obtain 0.6 g of a powdered mixture of ketoconazole and sucrose. The powdered mixture was dispersed into distilled water for measuring the particle size thereof with a particle size analyzer (Mastersizer Microplus). The results were shown in Table 1.

Example 3

20 g of cetyl alcohol and 1 g of ketoconazole were placed into a 250 ml volume beaker and heated to 80° C. with stirring until the mixture became completely melt to form a transparent liquid. After completely melting the mixture, additional stirring for about 10 minutes was further carried out for homogeneous mixing. Then, the melted mixture were poured into a stainless steel plate which was precooled to 10° C. or less for rapid cooling and solidifying, thereby obtaining the solid product in which the active ingredient was dispersed uniformly into the fat in the form of fine particles. The resulted solid product was milled into fine particles with about 100 μm particle size, by a domestic milling device, to provide fat powder. To the resulted fat powder, a solution of 1 g of sucrose as an anti-coagulating agent in 5 ml of water was added and stirred with a spatula for uniform mixing of the fat powder and the sucrose solution, thereby obtaining a mixture of the fat powder and sucrose. Since the resulted mixture of the fat powder and sucrose had small water content, it easily turned into a powder form. 13.5 g of the mixture of the fat powder and sucrose was placed into a pressure resistant reactor, and cetyl alcohol used as a solid fat was removed therefrom by the same method as in Example 1 to obtain 0.9 g of a powdered mixture of ketoconazole and sucrose. The powdered mixture was dispersed to distilled water for measuring the particle size thereof with a particle size analyzer (Mastersizer Microplus). The results were shown in Table 1.

Example 4

A mixture of a fat powder and sucrose was prepared by the same method as in Example 3, except that a solution of 2 g of sucrose as an anti-coagulating agent in 5 ml of water was added to 21 g of the fat powder comprised of ketoconazole and cetyl alcohol (1 g and 20 g, respectively). 10.4 g of the mixture of the fat powder and sucrose was placed into a pressure resistant reactor, and cetyl alcohol used as a solid fat was removed therefrom by the same method as in Example 1, thereby obtaining 1.0 g of a powdered mixture of ketoconazole and sucrose. The resulted powdered mixture was dispersed into distilled water for measuring the particle size with a particle size analyzer (Mastersizer Microplus). The results were shown in Table 1.

Example 5

A mixture of a fat powder and sucrose was prepared by the same method as in Example 3, except that a solution of 1 g of sucrose as an anti-coagulating agent in 8 ml of water was added to 21 g of the fat powder comprised of ketoconazole and cetyl alcohol (1 g and 20 g, respectively). 10.0 g of the mixture of the fat powder and sucrose was placed into a pressure resistant reactor, and cetyl alcohol used as a solid fat was removed therefrom by the same method as in Example 1, thereby obtaining 0.4 g of a powdered mixture of ketoconazole and sucrose with excellent flowability. The resulted powdered mixture was found to be adsorbed to the inner wall of the reactor in a significant amount. The resulted powdered mixture was dispersed into distilled water for measuring the particle size with a particle size analyzer (Mastersizer Microplus). The results were shown in Table 1.

TABLE 1

Average particle size (μm) of the final powders obtained from Examples 1-5

| | Raw material (Active ingredient) | Example 1 | Example 2 | Example 3 | Example 4 | Example 5 |
|---|---|---|---|---|---|---|
| Average particle size | 10.41 | 1.79 | 1.02 | 1.04 | 1.10 | 0.75 |

Example 6

A mixture of a fat powder, polyvinylpyrrolidone and sucrose was prepared by the same method as in Example 3, except that a solution of 0.1 g of polyvinylpyrrolidone (Polyvinylpyrrolidone K 30) as a surfactant and 1 g of sucrose as a non-surfactant type anti-coagulating agent in 8 ml of water, was added to 21 g of the fat powder comprised of ketoconazole and cetyl alcohol (1 g and 20 g, respectively). 10.0 g of the mixture of the fat powder, polyvinylpyrrolidone and sucrose was placed into a pressure resistant reactor, and cetyl alcohol used as a solid fat was removed therefrom by the same method as in Example 1, thereby obtaining 0.64 g of a powdered mixture of ketoconazole, sucrose and polyvinylpyrrolidone with excellent flowability. The resulted powdered mixture was found to be adsorbed to the inner wall of the reactor in a significant amount. The resulted powdered mixture was dispersed into distilled water for measuring the particle size with a particle size analyzer (Horiba LA910S). The results were shown in Table 2.

Example 7

A mixture of a fat powder and sucrose was prepared by the same method as in Example 3, except that the fat powder containing ketoconazole and polyvinylpyrrolidone dispersed uniformly therein as fine particles, was prepared by dissolving 0.1 g of polyvinylpyrrolidone and 1 g of ketoconazole together with 20 g of cetyl alcohol, and to the fat powder prepared above, a solution of 1 g of sucrose as an anti-coagulating agent in 8 ml of water was added. 10.0 g of the mixture of the fat powder and sucrose was placed into a pressure resistant reactor, and cetyl alcohol used as a solid fat was removed therefrom by the same method as in Example 1, thereby obtaining 0.62 g of a powdered mixture of ketoconazole, sucrose and polyvinylpyrrolidone with excellent flowability. The resulted powdered mixture was found to be adsorbed to the inner wall of the reactor in a significant amount. The resulted powdered mixture was dispersed into distilled water for measuring the particle size with a particle size analyzer (Horiba LA910S). The results were shown in Table 2.

Example 8

A fat powder containing ketoconazole and polyvinylpyrrolidone uniformly dispersed therein as fine particles was prepared by dissolving 0.1 g of polyvinylpyrrolidone and 1 g of ketoconazole together with 20 g of cetyl alcohol by the same method as in the Example 3. To the resulted fat powder, a solution of 1 g of sucrose as an anti-coagulating agent in 14 ml of water was added and mixed homogeneously. The resulted mixture was dried in a vacuum drier until the water content became 5% (w/w) or less relative to the amount of the cetyl alcohol. 9 g of the dried mixture prepared above was placed into a pressure resistant reactor, and cetyl alcohol was removed therefrom by the same method as in Example 1, thereby obtaining 0.8 g of a powdered mixture with excellent flowability. The resulted powdered mixture was dispersed into distilled water for measuring the particle size with a particle size analyzer (Horiba LA910S). The results were shown in Table 2.

Example 9

A mixture of a fat powder and sucrose was prepared by the same method as in Example 8, except that a solution of 2 g of sucrose as an anti-coagulating agent in 14 ml of water was added to the fat powder prepared by dissolving 0.1 g of polyvinylpyrrolidone and 1 g of ketoconazole together with 20 g of cetyl alcohol. Cetyl alcohol was removed from 9 g of the resulted mixture of the fat powder and sucrose by the same method as in Example 1, thereby obtaining 1.1 g of a powdered mixture with excellent flowability. The resulted powdered mixture was dispersed into distilled water for measuring the particle size with a particle size analyzer (Horiba LA910S). The results were shown in Table 2.

Example 10

A mixture of a fat powder and xylitol was prepared by the same method as in Example 8, except that a solution of 1 g of xylitol as an anti-coagulating agent in 14 ml of water was added to the fat powder prepared by dissolving 0.1 g of polyvinylpyrrolidone and 1 g of ketoconazole together with 20 g of cetyl alcohol. Cetyl alcohol was removed from 9 g of the resulted mixture of the fat powder and xylitol by the same method as in Example 1, thereby obtaining 0.8 g of a powdered mixture with excellent flowability. The resulted powdered mixture was dispersed into distilled water for measuring the particle size with a particle size analyzer (Horiba LA910S). The results were shown in Table 2.

Example 11

A mixture of a fat powder, xylitol, sodium dioctyl sulfosuccinate (DOSS) and sodium dodecylsulfate (SLS) was prepared by the same method as in Example 8, except that a solution of 1 g of xylitol as an anti-coagulating agent and 0.08 g of DOSS and 0.008 g of SLS as additional surfactants in 14 ml of water, was added to the fat powder prepared by dissolving 0.1 g of polyvinylpyrrolidone and 1 g of ketoconazole together with 20 g of cetyl alcohol. Cetyl alcohol was removed from 10 g of the resulted mixture of the fat powder, xylitol, DOSS and SLS by the same method as in Example 1, thereby obtaining 0.9 g of a powdered mixture with excellent flowability. The resulted powdered mixture was dispersed into distilled water for measuring the particle size with a particle size analyzer (Horiba LA910S). The results were shown in Table 2.

Example 12

0.25 g of polyvinylpyrrolidone and 1 g of ketoconazole were dissolved together with 20 g of cetyl alcohol, to prepare a fat powder containing ketoconazole and polyvinyl pyrrolidone uniformly dispersed therein as a form of fine particles. To the resulted fat powder, a solution of 1 g of xylitol as an anti-coagulating agent in 14 ml of water was added and mixed uniformly. Then, the mixture was dried in a vacuum drier until the water content became 5% (w/w) or less relative to the amount of cetyl alcohol. 9 g of the dried mixture prepared above was placed into a pressure resistant reactor, and cetyl alcohol was removed therefrom by the same method as in Example 1, thereby obtaining 0.88 g of a powdered mixture with excellent flowability. The resulted powdered mixture was dispersed into distilled water for measuring the particle size with a particle size analyzer (Horiba LA9105). The results were shown in Table 2.

Example 13

A fat powder containing ketoconazole and polyvinylpyrrolidone uniformly dispersed therein as fine particles, was prepared by dissolving 0.25 g of polyvinylpyrrolidone and 1 g of ketoconazole together with 20 g of cetyl alcohol by the same method as in Example 2. To the resulted fat powder, a solution of 1 g of sucrose as an anti-coagulating agent in 14 ml of water was added and mixed homogeneously. The resulted mixture was dried in a vacuum drier until the water content became 5% (w/w) or less relative to the amount of cetyl alcohol. 9 g of the dried mixture prepared above was placed into a pressure resistant reactor, and cetyl alcohol was removed therefrom by the same method as in Example 1, thereby obtaining 0.87 g of a powdered mixture with excellent flowability. The resulted powdered mixture was dispersed into distilled water for measuring the particle size with a particle size analyzer (Horiba LA910S). The results were shown in Table 2.

Example 14

A mixture of a fat powder, xylitol, DOSS and SLS was prepared by the same method as in Example 12, except that a solution of 1 g of xylitol as an anti-coagulating agent and 0.2 g of DOSS and 0.004 g of SLS as additional surfactants in 14 ml of water was added to the fat powder prepared by dissolving 0.25 g of polyvinylpyrrolidone and 1 g of ketoconazole together with 20 g of cetyl alcohol. Cetyl alcohol was removed from 9.06 g of the resulted mixture of the fat powder, xylitol, DOSS and SLS by the same method as in Example 1, thereby obtaining 0.96 g of a powdered mixture with excellent flowability. The resulted powdered mixture was dispersed into distilled water for measuring the particle size with a particle size analyzer (Horiba LA910S). The results were shown in Table 2.

Example 15

A mixture of a fat powder and sucrose was prepared by the same method as in Example 3, except that the fat powder containing ketoconazole and sucrose fatty acid ester uniformly dispersed therein as fine particles was prepared by dissolving 0.13 g of sucrose fatty acid ester and 1 g of ketoconazole together with 20 g of cetyl alcohol by the same method as in Example 2, and to the fat powder prepared above, a solution of 1 g of sucrose as an anti-coagulating agent in 9 ml of water was added. 9.0 g of the mixture of the fat powder and sucrose was placed into a pressure resistant reactor, and cetyl alcohol used as a solid fat was removed therefrom by the same method as in Example 1, thereby obtaining 1.18 g of a powdered mixture of sucrose fatty acid ester, sucrose and ketoconazole with excellent flowability. The resulted powdered mixture was dispersed into distilled water for measuring the particle size with a particle size analyzer (Horiba LA910S). The results were shown in Table 2.

Example 16

A fat powder containing ketoconazole and sucrose fatty acid ester uniformly dispersed therein as fine particles was prepared by dissolving 0.25 g of sucrose fatty acid ester and 1 g of ketoconazole together with 20 g of cetyl alcohol by the same method as in Example 2. To the resulted fat powder, a solution of 1 g of sucrose as an anti-coagulating agent in 14 ml of water was added and mixed homogeneously. The resulted mixture was dried in a vacuum drier until the water content became 5% (w/w) or less relative to the amount of cetyl alcohol. 10 g of the dried mixture prepared above was placed into a pressure resistant reactor, and cetyl alcohol was removed therefrom by the same method as in Example 1, thereby obtaining 0.89 g of a powdered mixture with excellent flowability. The resulted powdered mixture was dispersed into distilled water for measuring the particle size with a particle size analyzer (Horiba LA910S). The results were shown in Table 2.

Example 17

A fat powder containing ketoconazole and sucrose fatty acid ester uniformly dispersed therein as fine particles, was prepared by dissolving 0.25 g of sucrose fatty acid ester and 1 g of ketoconazole together with 20 g of cetyl alcohol by the same method as in Example 2. To the resulted fat powder, a solution of 1 g of xylitol as an anti-coagulating agent in 14 ml of water was added and mixed homogeneously. The resulted mixture was dried in a vacuum drier until the water content became 5% (w/w) or less relative to the amount of cetyl alcohol. 10 g of the dried mixture prepared above was placed into a pressure resistant reactor, and cetyl alcohol was removed therefrom by the same method as in Example 1, thereby obtaining 0.87 g of a powdered mixture with excellent flowability. The resulted powdered mixture was dispersed into distilled water for measuring the particle size with a particle size analyzer (Horiba LA910S). The results were shown in Table 2.

Example 18

A fat powder containing lovastatin and polyvinylpyrrolidone uniformly dispersed therein as fine particles, was prepared by dissolving 0.25 g of polyvinylpyrrolidone and 1 g of lovastatin together with 20 g of cetyl alcohol by the same method as in Example 2. To the resulted fat powder, a solution of 1 g of xylitol as an anti-coagulating agent in 14 ml of water was added and mixed homogeneously. The resulted mixture was dried in a vacuum drier until the water content became 5% (w/w) or less relative to the amount of cetyl alcohol. 10 g of the dried mixture prepared above was placed into a pressure resistant reactor, and cetyl alcohol was removed therefrom by the same method as in Example 1, thereby obtaining 0.85 g of a powdered mixture with excellent flowability. The resulted powdered mixture was dispersed into distilled water for measuring the particle size with a particle size analyzer (Horiba LA910S). The results were shown in Table 2.

Example 19

A fat powder containing paclitaxel and polyvinylpyrrolidone uniformly dispersed therein as fine particles, was prepared by dissolving 0.25 g of polyvinylpyrrolidone and 1 g of paclitaxel together with 20 g of cetyl alcohol by the same method as in Example 2. To the resulted fat powder, a solution of 1 g of xylitol as an anti-coagulating agent in 14 ml of water was added and mixed homogeneously. The resulted mixture was dried in a vacuum drier until the water content became 5% (w/w) or less relative to the amount of cetyl alcohol. 10 g of the dried mixture prepared above was placed into a pressure resistant reactor, and cetyl alcohol was removed therefrom by the same method as in Example 1, thereby obtaining 1.02 g of a powdered mixture with excellent flowability. The resulted powdered mixture was dispersed into distilled water for measuring the particle size with a particle size analyzer (Horiba LA910S). The results were shown in Table 2.

Example 20

A fat powder containing itraconazole and polyvinylpyrrolidone uniformly dispersed therein as fine particles, was prepared by dissolving 0.25 g of polyvinylpyrrolidone and 1 g of itraconazole together with 20 g of cetyl alcohol by the same method as in Example 2. To the resulted fat powder, a solution of 1 g of xylitol as an anti-coagulating agent in 14 ml of water, was added and mixed homogeneously. The resulted mixture was dried in a vacuum drier until the water content became 5% (w/w) or less relative to the amount of cetyl alcohol. 10 g of the dried mixture prepared above was placed into a pressure resistant reactor, and cetyl alcohol was removed therefrom by the same method as in Example 1, thereby obtaining 1.05 g of a powdered mixture with excellent flowability. The resulted powdered mixture was dispersed into distilled water for measuring the particle size with a particle size analyzer (Horiba LA910S). The results were shown in Table 2.

TABLE 2

Particle size distribution(μm) of the final powdered mixtures obtained from Examples 6-20

| Example | D50 | D70 | D90 | Average |
|---|---|---|---|---|
| 6 | 0.4796 | 0.6785 | 1.0873 | 0.5941 |
| 7 | 0.4678 | 0.6346 | 1.1100 | 0.7205 |
| 8 | 0.4787 | 0.6983 | 1.4772 | 0.9289 |
| 9 | 0.5114 | 0.7515 | 1.3731 | 0.7695 |
| 10 | 0.5045 | 0.7341 | 1.3185 | 0.7565 |
| 11 | 0.5966 | 0.8978 | 1.4914 | 0.8793 |
| 12 | 0.4528 | 0.6064 | 1.0082 | 0.6542 |
| 13 | 0.4630 | 0.6223 | 1.0392 | 0.6603 |
| 14 | 0.5061 | 0.6921 | 1.0850 | 0.6191 |
| 15 | 0.5243 | 0.7500 | 1.2812 | 0.9024 |
| 16 | 0.5278 | 0.8728 | 1.6520 | 0.8335 |
| 17 | 0.5702 | 0.8982 | 1.5235 | 0.7759 |
| 18 | 0.4452 | 0.6164 | 1.0012 | 0.5954 |
| 19 | 0.4764 | 0.6074 | 1.0068 | 0.6052 |
| 20 | 0.5164 | 0.6257 | 1.1200 | 0.7021 |

INDUSTRIAL AVAILABILITY

According to the present invention, nanoscale or amorphous fine particles of active ingredients are obtained, by removing solid fats from a mixture comprising active ingredients and solid fats with a supercritical fluid. The nanoparticles prepared by the present invention may be suitably used in medicinal products, functional or general foods, cosmetics and the like, due to their excellent dispersability, absorbing property, physiological activity and the like.

What is claimed is:

1. A method for preparing nanoscale particles comprising the steps of:
   (1) preparing a mixture comprising one or more active ingredients and solid fat as a solvent in an excess amount to the active ingredient, and
   (2) pressurizing the mixture comprising one or more active ingredients and solid fat to the critical pressure or more by adding the gas of a supercritical fluid into the mixture, then removing the solid fat from the mixture by releasing out the solid fat together with the gas of the supercritical fluid, wherein the supercritical fluid is $CO_2$ or $N_2$ and wherein the temperature is maintained below the melting point of the solid fat; and
   wherein the step (1) comprises adding one or more active ingredients, solid fat and optionally one or more surfactants into a reactor and melt-mixing them homogeneously.

2. The method for preparing nanoscale particles according to claim 1, wherein the step (1) further comprises rapidly cooling the homogeneously melt-mixed mixture for solidification by pouring the mixture into a stainless steel plate which was pre-cooled to 10° C. or less; pulverizing the solidified mixture; adding one or more surfactants and/or one or more non-surfactant type anti-coagulating agents or aqueous solution thereof to the pulverized powder and mixing them homogeneously; and drying the mixed product at room temperature.

3. A method for preparing nanoscale particles comprising the steps of:
   (1) preparing a mixture comprising one or more active ingredients and solid fat as a solvent in an excess amount to the active ingredient, and
   (2) pressurizing the mixture comprising one or more active ingredients and solid fat to the critical pressure or more by adding the gas of a supercritical fluid into the mixture, and then removing the solid fat from the mixture by releasing out the solid fat together with the gas of the supercritical fluid, wherein the supercritical fluid is $CO_2$ or $N_2$ and wherein the temperature is maintained below the melting point of the solid fat,
   wherein the step (1) comprises: adding one or more surfactants and solid fat into a reactor, and melt-mixing them homogenously; rapidly cooling the homogenously melt-mixed mixture for solidification by pouring the mixture into a stainless steel plate which was pre-cooled to 10° C. or less; pulverizing the solidified mixture; adding one or more surfactants and/or one or more non-surfactant type anti-coagulating agents together with one or more active ingredients or aqueous solution thereof, to the pulverized powder and mixing them homogenously; and drying the mixed product at room temperature.

4. The method for preparing nanoscale or particles according to claim 1, wherein the step (1) comprises: adding one or more active ingredients, solid fat and optionally one or more surfactants into a reactor, further adding the gas of a supercritical fluid so as to provide a subcritical or supercritical condition, and then melt-mixing the mixture by heating.

5. The method for preparing nanoscale particles according to claim 1, wherein the step (1) comprises: adding one or more active ingredients, solid fat and optionally one or more surfactants into a reactor, pressurizing the mixture to the critical pressure or more by adding the gas of a supercritical fluid into the mixture and then melt-mixing the mixture by heating, and spraying the melted mixture to the atmospheric pressure.

6. The method for preparing nanoscale particles according to claim 1, wherein the step (1) comprises: adding one or more active ingredients, solid fat and optionally one or more surfactants into a reactor, pressurizing the mixture to the critical pressure or more by adding the gas of a supercritical fluid and then melt-mixing the mixture by heating, and then pulverizing the melted mixture by spraying it to the atmospheric pressure; adding one or more surfactants and/or one or more non-surfactant type anti-coagulating agents or aqueous solution thereof to the pulverized mixture and mixing them homogeneously; and drying the mixture at room temperature.

7. The method for preparing nanoscale particles according to claim 1 or 3, wherein the active ingredient is organic compounds, organometallic compounds, natural extracts, peptides, proteins or polysaccharides that exhibits physiological activities.

8. The method for preparing nanoscale particles according to claim 1 or 3, wherein the solid fat is a fat or a mixture of fats maintaining solid phase at the temperature of 30° C. or less and having a melting point of 40-150° C.

9. The method for preparing nanoscale particles according to claim 8, wherein the solid fat is selected from the group consisting of saturated fatty acids, esters and alcohols with C10-C22; mono- or di-glycerides having saturated fatty acid group with C10-C22; hydrocarbons with C16 or more; triglycerides having saturated fatty acid group with C10-C22; and a mixture thereof.

10. The method for preparing nanoscale particles according to claim 1 or 3, wherein the mixture prepared from the step (1) further comprises one or more material selected from the group consisting of synthetic surfactants, natural surfactants, lipids, polymers, monosaccharides, polysaccharides, dietary fibers, gums and proteins.

11. The method for preparing nanoscale particles according to claim 1 or 3, wherein the surfactant is at least one selected from the group consisting of synthetic surfactants, natural surfactants, lipids and polymers.

12. The method for preparing nanoscale particles according to claim 2 or 3, wherein the non-surfactant type anti-coagulating agent is at least one selected from the group consisting of monosaccharides, polysaccharides, dietary fibers, gums and proteins.

13. The method for preparing nanoscale particles according to claim 1 or 3, wherein the mixture prepared in the step (1) further comprises a co-solvent.

14. The method for preparing nanoscale particles according to claim 13, wherein the co-solvent is one or more alcohols with C2-C6.

15. The method for preparing nanoscale particles according to claim 1 or 3, wherein the temperature inside the reactor in the step (2) is 20-40° C.

16. The method for preparing nanoscale particles according to claim 1 or 3, wherein, in the step (2), the solid fat is removed from the mixture comprising one or more active ingredients and solid fat under 70-400 atm by adding the gas of the supercritical fluid to the mixture.

17. The method for preparing nanoscale particles according to claim 6, wherein the non-surfactant type anti-coagulating agent is at least one selected from the group consisting of monosaccharides, polysaccharides, dietary fibers, gums and proteins.

* * * * *